United States Patent [19]
Murugesan et al.

[11] Patent Number: 5,939,446
[45] Date of Patent: Aug. 17, 1999

[54] HETEROARYL SUBSTITUTED PHENYL ISOXAZOLE SULFONAMIDE ENDOTHELIN ANTAGONISTS

[75] Inventors: Natesan Murugesan, Princeton Junction, N.J.; Joel C. Barrish, Holland, Pa.

[73] Assignee: Bristol-Myers Squibb Co., Princeton, N.J.

[21] Appl. No.: 08/821,503

[22] Filed: Mar. 21, 1997

Related U.S. Application Data

[60] Provisional application No. 60/015,072, Apr. 9, 1996.

[51] Int. Cl.⁶ .......................... A61K 31/42; A61K 31/505; C07D 261/14; C07D 239/24
[52] U.S. Cl. .......................... 514/380; 514/252; 514/256; 514/340; 514/379; 544/238; 544/333; 546/272.1; 548/241; 548/246
[58] Field of Search ..................................... 514/252, 256, 514/340, 379, 380; 544/238, 333; 546/272.1; 548/241, 246

[56] References Cited

U.S. PATENT DOCUMENTS

| | | | |
|---|---|---|---|
| 2,888,455 | 5/1959 | Kano et al. | 260/239.9 |
| 4,415,496 | 11/1983 | Harris et al. | 260/239.3 |
| 4,661,479 | 4/1987 | Wyvratt, Jr. et al. | 514/214 |
| 5,236,928 | 8/1993 | Chakravarty et al. | 514/275 |
| 5,270,313 | 12/1993 | Burri et al. | 514/252 |
| 5,292,740 | 3/1994 | Burri et al. | 514/256 |
| 5,378,715 | 1/1995 | Stein et al. | 514/329 |
| 5,464,853 | 11/1995 | Chan et al. | 514/378 |
| 5,514,691 | 5/1996 | Chan et al. | 514/312 |
| 5,514,696 | 5/1996 | Murugesan et al. | 514/380 |
| 5,571,821 | 11/1996 | Chan et al. | 514/312 |
| 5,591,761 | 1/1997 | Chan et al. | 514/380 |
| 5,594,021 | 1/1997 | Chan et al. | 514/378 |
| 5,612,359 | 3/1997 | Murugesan | 514/365 |
| 5,760,038 | 6/1998 | Murugesan et al. | 514/252 |
| 5,780,473 | 7/1998 | Murugesan et al. | 514/252 |

FOREIGN PATENT DOCUMENTS

| | | |
|---|---|---|
| 34011/93 | 9/1993 | Australia . |
| 67357/94 | 1/1995 | Australia . |
| 48039/96 | 9/1996 | Australia . |
| 76072 | 4/1983 | European Pat. Off. . |
| 194548 | 9/1986 | European Pat. Off. . |
| 404525 | 12/1990 | European Pat. Off. . |
| 443983 | 8/1991 | European Pat. Off. . |
| 510526 | 10/1992 | European Pat. Off. . |
| 526708 | 2/1993 | European Pat. Off. . |
| 5588258 | 9/1993 | European Pat. Off. . |
| 569193 | 11/1993 | European Pat. Off. . |
| 601386 | 6/1994 | European Pat. Off. . |
| 617001 | 9/1994 | European Pat. Off. . |
| 626174 | 11/1994 | European Pat. Off. . |
| 633259 | 1/1995 | European Pat. Off. . |
| 634175 | 1/1995 | European Pat. Off. . |
| 640596 | 3/1995 | European Pat. Off. . |
| 682016 | 11/1995 | European Pat. Off. . |
| 702012 | 3/1996 | European Pat. Off. . |
| 725067 | 8/1996 | European Pat. Off. . |
| 749964 | 12/1996 | European Pat. Off. . |
| 1059459 | 6/1959 | Germany . |
| 0364506 | 11/1962 | Switzerland . |
| 804036 | 11/1958 | United Kingdom . |
| 0897440 | 5/1962 | United Kingdom . |
| 1473433 | 5/1977 | United Kingdom . |
| 2228933 | 9/1990 | United Kingdom . |
| 91/15479 | 10/1991 | WIPO . |
| 93/08799 | 5/1993 | WIPO . |
| 93/10094 | 5/1993 | WIPO . |
| 93/23404 | 11/1993 | WIPO . |
| 94/27979 | 12/1994 | WIPO . |
| 95/26957 | 10/1995 | WIPO . |
| 96/31492 | 10/1996 | WIPO . |
| 96/40681 | 12/1996 | WIPO . |

OTHER PUBLICATIONS

S. Norio et al., Chemical Abstracts, vol. 70, No. 19, (1969), 87639g.
T. Saito, Chemical Abstracts, vol. 73, No. 23 (1970), 120511w.
Derwent Abstract No. 88–289069/41 Feb. 27, 1987.
Derwent Abstract No. 88–195835/28 Nov. 26, 1986.
Derwent Abstract No. 88–061295/09 Jul. 9, 1986.
Derwent Abstract No. 87–152485/22 Oct. 11, 1985.
Derwent Abstract No. 62299 E/30 Dec. 11, 1980.
Derwent Abstract No. 40927 D/23 Sep. 11, 1979.
Derwent Abstract No. 91–254550/35 Feb. 19, 1990.
Derwent Abstract No. 86–246709/38 Nov. 27, 1985.
Derwent Abstract No. 35012 K/15 Sep. 24, 1981.
Allen et al., "Preparation . . . antagonists", CA116(11):106284Z, p. 778, 1992.
R.D. Desai et al., Chemical Abstracts, vol. 71, No. 11, (1969) 49825c.
R.D. Desai et al., Chemical Abstracts, vol. 71, No. 3, (1969) 12872q.
P. G. Ferrini et al., Angew. Chem. Internat. Edit., vol. 2, No. 2 (1963) p. 99.
A. M. van Leusen, et al., "Synthesis . . . Compounds", J. Org. Chem., vol. 41, No. 4, (1976), pp. 69–71.
W. J. Hammar et al., J. Heterocyclic Chem., vol. 18, (1981) pp. 885–888.

(List continued on next page.)

Primary Examiner—Richard L. Raymond
Assistant Examiner—Brenda Coleman
Attorney, Agent, or Firm—Suzanne E. Babajko; Stephen B. Davis

[57] ABSTRACT

Compounds of the formula

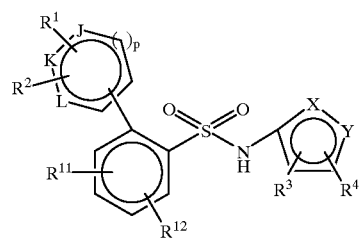

inhibit the activity of endothelin.

18 Claims, No Drawings

OTHER PUBLICATIONS

A. M. van Leusen et al., Tetrahedron Letters, No. 23, (1972), pp. 2369–2372.

Chan et al., "Identification of a New Class of $ET_A$ Selective Endothelin Antagonists by Pharmacophore Directed Screening", Biochemical and Biophysical Research Communications, vol. 201, No. 1, May 30, 1994, pp. 228–234.

Stein et al., "The Discovery of Sulfonamide Endothelin Antagonists and the Development of the Orally Active $ET_A$ Antagonist 5-(Dimethylamino)-N-(3, 4-dimethyl-5-isoxazolyl)-1-naphthalenesulfonamide", J. Med. Chem., vol. 37, No. 3, Feb. 4, 194, pp. 329–331.

Doherty, J. Med. Chem., 35(9), 1493–1508 (May 1992).

CA 65: 2241d (1966).

CA 92:41908v (1979).

Wang et al., "Nitrile . . . sinomin," CA 108:94444w, p. 651 (1988).

Khanna, "Oral . . . formulation," CA 115:35728p, p. 415 (1991).

Stein et al., "The Discovery . . . 1-naphthalenesulfonamide," CA 120:18233n, pp. 21–22 (1994).

Vree et al., "Renal excretion . . . function," CA 97:84685r, p. 23 (1982).

Oie, "Pharmacokinetics . . . dosing," CA 102:197512x, p. 18 (1985).

Murugesan et al., "N-(heteroaryl) . . . antagonists," CA 120:270370c, p. 1067 (1994).

Chan et al., Am. J. Physiol., "Effect of an endothelin-receptor antagonist on ischemic acute renal failure", 1994, vol. 266, pp. F135–F138.

Marsen et al., "Renal actions of endothelin . . . " Kidney Int., 1994, vol. 45, pp. 336–344.

Mitaka et al., "Endothelin-1 and atrial natriuretic peptide in septic shock", Am. Heart J., 1993, vol. 126, pp. 466–468.

Hirata et al., "Plasma Endothelins in Sepsis Syndrome", JAMA, 1993, vol. 270, p. 2182.

Battistini et al., "Growth Regulatory Properties of Endothelins", Peptides, 1993, vol. 14, pp. 385–399.

Ohlstein et al., "The selective endothelin $ET_A$ . . . ", Eur. J. Pharmcol., 1992, vol. 225, pp. 347–350.

Winkles et al., "Endothelin-1 and Endothelin Receptor . . . ", Biochem. Biophys. Res. Comm., 1993, vol. 191, pp. 1081–1088.

Kowala, "Endothelin receptors and atherosclerosis . . .", Exp. Opin. Invest. Drugs, 1996, vol. 5, pp. 1495–1508.

Kowala et al., "Selective Blockade of the Endothelin Subtype A . . . ", Am. J. Pathol., 1995, vol. 146, pp. 819–826.

Lerman et al., "Circulating And Tissue Endothelin . . . ", 1991, vol. 325, pp. 997–1001.

Douglas et al., "A Role for Endogenous Endothelin-1 . . . ", Circ. Res., 1994, vol. 75, pp. 190–197.

Tahara et al., "Ciculating Immunoreactive Endothelin . . . ", Metabolism, 1991, vol. 40, pp. 1235–1237.

Kobayashi et al., "Localization Of Endothelin Receptors In The Human Prostrate", J. Urol., 1991, vol. 151, pp. 763–766.

Kobayashi et al, "Binding and Functional Properties of Endothelin . . . " Mol. Pharmcol., 1994, vol. 45, pp. 306–311.

Kiowski et al., "Evidence of Endothelin-1 mediated vasoconstriction . . . ", Lancet, 195, vol. 346, pp. 732–736.

Sakai et al., "Inhibition of myocardial endothelin pathway . . . ", Nature, 1996, vol. 384, pp. 353–355.

Bradbury et al., New Non-Peptide Edothelin-A Receptor Antagonists: Synthesis, Biological Properties, and Structure-Activity Relationships of 5-(Dimethylamino)-N-Pyridyl, -N-Pyrimidinyl-, -N-Pyridazinyl-, and -N-Pyrazinyl-1-Naphthalenesulfonamides, Journa, Mar. 1997.

Stein et al., Discovery and Structure-Activity Relationships of Sulfonamide ETA-Selective Antagonists, Journal of Medicinal Chemistry, vol. 38, pp. 1344–1354, 1995.

HETEROARYL SUBSTITUTED PHENYL ISOXAZOLE SULFONAMIDE ENDOTHELIN ANTAGONISTS

This application claims priority from provisional U.S. Application Ser. No. 60/015,072, filed Apr. 9, 1996, incorporated herein by reference in its entirety.

FIELD OF THE INVENTION

This invention relates to endothelin antagonists useful, inter alia, for treatment of hypertension.

BRIEF DESCRIPTION OF THE INVENTION

Compounds of the formula

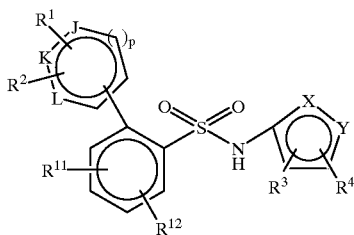

I its enantiomers and diastereomers, and pharmaceutically acceptable salts thereof are endothelin receptor antagonists useful, inter alia, as antihypertensive agents. Throughout this specification, the above symbols are defined as follows:
one of X and Y is N and the other is O;
$R^1$, $R^2$, $R^3$ and $R^4$ are each directly bonded to a ring carbon and are each independently
  (a) hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
  (c) halo;
  (d) hydroxyl;
  (e) cyano;
  (f) nitro;
  (g) —C(O)H or —C(O)$R^5$;
  (h) —CO$_2$H or —CO$_2R^5$;
  (i) -$Z^4$-NR$^6$R$^7$;
  (j) -$Z^4$-N($R^{10}$)-$Z^5$-NR$^8$R$^9$; or
  (k) $R^3$ and $R^4$ together may also be alkylene or alkenylene, either of which may be substituted with $Z^1$, $Z^2$ and $Z^3$, completing a 4- to 8-membered saturated, unsaturated or aromatic ring together with the carbon atoms to which they are attached;
$R^5$ is alkyl, alkenyl, alkynyl, cycloalkyl, cycloalkylalkyl, cycloalkenyl, cycloalkenylalkyl, aryl or aralkyl, any of which may be substituted with $Z^1$, $Z^2$ and $Z^3$;
$R^6$, $R^7$, $R^8$, $R^9$ and $R^{10}$ are each independently
  (a) hydrogen; or
  (b) alkyl, cycloalkyl, cycloalkylalkyl, cycloalkenylalkyl, aryl or aralkyl, any of which may be substituted with $Z^1$, $Z^2$ and $Z^3$; or
$R^6$ and $R^7$ together may be alkylene or alkenylene, either of which may be substituted with $Z^1$, $Z^2$ and $Z^3$, completing a 3- to 8-membered saturated or unsaturated ring together with the nitrogen atom to which they are attached; or any two of $R^8$, $R^9$ and $R^{10}$ together are alkylene or alkenylene, either of which may be substituted with $Z^1$, $Z^2$ and $Z^3$, completing a 3- to 8-membered saturated or unsaturated ring together with the atoms to which they are attached;
$R^{11}$ and $R^{12}$ are each independently
  (a) hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$,
  (c) heterocycle, substituted heterocycle or heterocyclooxy;
  (d) halo;
  (e) hydroxyl;
  (f) cyano;
  (g) nitro;
  (h) —C(O)H or —C(O)$R^5$;
  (i) —CO$_2$H or —CO$_2R^5$;
  (j) —SH, —S(O)$_n$R$^5$, —S(O)$_m$—OH, —S(O)$_m$—OR$^5$, —O—S(O)$_m$—OR$^5$, —O—S(O)$_m$OH or —O—S(O)$_m$—OR$^5$;
  (k) -$Z^4$-NR$^6$R$^7$; or
  (l) -$Z^4$-N($R^{10}$)-$Z^5$-NR$^8$R$^9$;
$Z^1$, $Z^2$ and $Z^3$ are each independently
  (a) hydrogen;
  (b) halo;
  (c) hydroxy;
  (d) alkyl;
  (e) alkenyl;
  (f) aryl;
  (g) aralkyl;
  (h) alkoxy;
  (i) aryloxy;
  (j) aralkoxy;
  (k) heterocycle, substituted heterocycle or heterocyclooxy;
  (l) —SH, —S(O)$_n$Z$^6$, —S(O)$_m$—OH, —S(O)$_m$—OZ$^6$, —O—S(O)$_m$-Z$^6$, —O—S(O)$_m$OH or —O—S(O)$_m$—OZ$^6$;
  (m) oxo;
  (n) nitro;
  (o) cyano;
  (p) —C(O)H or —C(O)Z$^6$;
  (q) —CO$_2$H or —CO$_2$Z$^6$;
  (r) -$Z^4$-NZ$^7$Z$^8$;
  (s) -$Z^4$-N($Z^{11}$)-$Z^5$-H;
  (t) -$Z^4$-N($Z^{11}$)-$Z^5$-Z$^6$; or
  (u) -$Z^4$-N($Z^{11}$)-$Z^5$-NZ$^7$Z$^8$;
$Z^4$ and $Z^5$ are each independently
  (a) a single bond;
  (b) -$Z^9$-S(O)$_n$-$Z^{10}$-;
  (c) -$Z^9$-C(O)-$Z^{10}$-;
  (d) -$Z^9$-C(S)-$Z^{10}$-;
  (e) -$Z^9$-O-$Z^{10}$-;
  (f) -$Z^9$-S-$Z^{10}$-;
  (g) -$Z^9$-O—C(O)-$Z^{10}$-; or
  (h) -$Z^9$-C(O)—O-$Z^{10}$-;
$Z^6$ is alkyl; alkyl substituted with one to three groups selected from halogen, aryl, aryloxy and alkoxy; alkenyl;

alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy and trihaloalkoxy; or heterocycle or substituted heterocycle;

$Z^7$ and $Z^8$ are each independently hydrogen, alkyl, cycloalkyl, cycloalkylalkyl, cycloalkenylalkyl, aryl or aralkyl, or $Z^7$ and $Z^8$ together are alkylene or alkenylene, completing a 3- to 8-membered saturated or unsaturated ring together with the nitrogen atom to which they are attached;

$Z^9$ and $Z^{10}$ are each independently a single bond, alkylene, alkenylene or alkynylene;

$Z^{11}$ is (a) hydrogen; or (b) alkyl, alkyl substituted with one, two or three halogens, cycloalkyl, cycloalkylalkyl, cycloalkenylalkyl, aryl or aralkyl;

or any two of $Z^7$, $Z^8$ and $Z^{11}$ together are alkylene or alkenylene, completing a 3- to 8-membered saturated or unsaturated ring together with the atoms to which they are attached;

each m is independently 1 or 2;

each n is independently 0, 1 or 2;

p is 0 or 1; and when p is 0, then J is N, $NR^{13}$ or S; K and L are each —C; $R^{13}$ is H, alkyl or —$SO_2R^{14}$; and $R^{14}$ is aryl; and $R^1$ and $R^2$ together may also be alkylene or alkenylene, either of which may be substituted with $Z^1$, $Z^2$ and $Z^3$, completing a 4- to 8-membered saturated, unsaturated or aromatic ring together with the atoms to which they are attached; or when p is 1, then J, K and L are each, independently, —C or N, provided that at least one of J, K and L is —C and at least one of J, K and L is N.

For compound I, it is preferred that at least one, or most preferably all, of the substituent groups are as follows:

X is O and Y is N;

$R^3$ and $R^4$ are each independently alkyl, most preferably, methyl;

$R^{11}$ and $R^{12}$ are each independently hydrogen, hydroxy, amino, alkenyl, carboxamide or substituted lower alkyl, most preferably, hydrogen;

when p is 0, then J is N or $NR^{13}$, most preferably, where $R^{13}$ is hydrogen or phenylsulfonyl, and $R^1$ and $R^2$ together are alkenylene, completing a 6-membered aromatic ring; or J is S, and $R^1$ and $R^2$ are hydrogen; and when p is 1, then $R^1$ and $R^2$ are each independently hydrogen, alkyl, alkoxy, aryl, hydroxyalkyl, —$CO_2R^5$ or -$Z^4$—$NR^6R^7$, most preferably, hydrogen.

Particularly preferred compounds include those of the Examples of the present specification.

DETAILED DESCRIPTION OF THE INVENTION

Listed below are definitions of terms used in this specification. These definitions apply to the terms as used throughout this specification, individually or as part of another group, unless otherwise indicated in specific instances.

The term "alkyl" or "alk-" refers to straight or branched chain hydrocarbon groups having 1 to 10 carbon atoms, preferably 1 to 7 carbon atoms. The expression "lower alkyl" refers to alkyl groups of 1 to 4 carbon atoms.

The term "alkoxy" refers to alkyl-O—. The term "lower alkoxy" refers to lower alkyl-O—.

The term "aryl" or "ar-" refers to phenyl, naphthyl and biphenyl.

The term "alkenyl" refers to straight or branched chain hydrocarbon groups of 2 to 10 carbon atoms having at least one double bond. Groups of two to four carbon atoms are preferred.

The term "alkynyl" refers to straight or branched chain groups of 2 to 10 carbon atoms having at least one triple bond. Groups of two to four carbon atoms are preferred.

The term "alkylene" refers to a straight chain bridge of 1 to 5 carbon atoms connected by single bonds (e.g., —($CH_2$)$_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —$CH_2$—CH=CH—, —$CH_2$—CH=CH—$CH_2$—, —C($CH_3$)$_2$CH=CH— and —CH($C_2H_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —$CH_2$—C≡C—, —CH($CH_3$)—C≡C— and —C≡C—CH($C_2H_5$)$CH_2$—.

The term "alkanoyl" refers to groups of the formula —C(O)alkyl.

The terms "cycloalkyl" and "cycloalkenyl" refer to cyclic hydrocarbon groups of 3 to 8 carbon atoms.

The term "hydroxyalkyl" refers to an alkyl group including one or more hydroxy radicals such as —$CH_2CH_2OH$, —$CH_2CHOHCH_2OH$, —CH($CH_2OH$)$_2$ and the like.

The terms "halogen" and "halo" refer to fluorine, chlorine, bromine and iodine.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms or sulfur atoms, where the nitrogen and sulfur heteroatoms may optionally be oxidized and the nitrogen heteroatoms may optionally be quaternized. The heterocyclic group may be attached at any heteroatom or carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

The expression "substituted heterocycle" refers to a heterocycle substituted with 1, 2 or 3 of the following:

(a) alkyl, especially lower alkyl;
(b) hydroxy (or protected hydroxy);
(c) halo;
(d) oxo (i.e. =O);
(e) amino, alkylamino or dialkylamino;
(f) alkoxy;
(g) carbocyclo, such as cycloalkyl;
(h) carboxy;
(i) heterocyclooxy;
(j) alkoxycarbonyl, such as unsubstituted lower alkoxycarbonyl;
(k) carbamyl, alkylcarbamyl or dialkylcarbamyl;
(l) mercapto;
(m) nitro;
(n) cyano;
(o) carboalkoxy;
(p) sulfonamido, sulfonamidoalkyl or sulfonamidodialkyl;
(q)

(r)

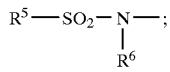

(s) aryl;
(t) alkylcarbonyloxy;
(u) arylcarbonyloxy;
(v) arylthio;
(w) aryloxy;
(x) alkylthio;
(y) formyl;
(z) arylalkyl; or
(a') aryl substituted with alkyl, cycloalkyl, alkoxy, hydroxy, amino, alkylamino, dialkylamino, halo or trihaloalkyl.

The term "heterocyclooxy" denotes a heterocyclic group bonded through an oxygen bridge.

Throughout the specification, groups and substituents thereof are chosen to provide stable moieties and compounds.

The compounds of formula I form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, t-butyl amine, benzathine, N-methyl-D-glucamide and hydrabamine, and with amino acids such as arginine, lysine and the like. Such salts may be obtained by reacting compound I with the desired ion in a medium in which the salt precipitates or in an aqueous medium followed by lyophilization.

When the $R^1$ to $R^4$ or $R^{11}$ to $R^{12}$ substituents comprise a basic moiety, such as amino or substituted amino, compound I may form salts with a variety of organic and inorganic acids. Such salts include those formed with hydrochloric acid, hydrogen bromide, methanesulfonic acid, sulfuric acid, acetic acid, maleic acid, benzenesulfonate, toluenesulfonate and various other sulfonates, nitrates, phosphates, borates, acetates, tartrates, maleates, citrates, succinates, benzoates, ascorbates, salicylates and the like. Such salts may be formed by reacting compound I in an equivalent amount of the acid in a medium in which the salt precipitates or in an aqueous medium followed by lyophilization.

In addition, when the $R^1$ to $R^4$ or $R^{11}$ to $R^{12}$ substituents comprise a basic moiety such as amino, zwitterions ("inner salts") may be formed.

The $R^1$ to $R^4$ and $R^{11}$ to $R^{12}$ substituents of compound I may contain asymmetric carbon atoms. Such compounds of formula I may exist, therefore, in enantiomeric and diastereomeric forms and in racemic mixtures thereof. All are within the scope of this invention. Additionally, compound I may exist as enantiomers even in the absence of asymmetric carbons. All such enantiomers are within the scope of this invention.

The compounds of formula I are antagonists of ET-1, ET-2 and/or ET-3 and are useful in treatment of conditions associated with increased ET levels (e.g., dialysis, trauma and surgery) and of all endothelin-dependent disorders. They are thus useful as antihypertensive agents. By the administration of a composition having one (or a combination) of the compounds of this invention, the blood pressure of a hypertensive mammalian (e.g., human) host is reduced. They are also useful in pregnancy-induced hypertension and coma (preeclampsia and eclampsia), acute portal hypertension and hypertension secondary to treatment with erythropoietin.

The compounds of the present invention are also useful in the treatment of disorders related to renal, glomerular and mesangial cell function, including acute and chronic renal failure, glomerular injury, renal damage secondary to old age or related to dialysis, nephrosclerosis (especially hypertensive nephrosclerosis), nephrotoxicity (including nephrotoxicity related to imaging and contrast agents and to cyclosporine), renal ischemia, primary vesicoureteral reflux, glomerulosclerosis and the like. The compounds of this invention may also be useful in the treatment of disorders related to paracrine and endocrine function.

The compounds of the present invention are also useful in the treatment of endotoxemia or endotoxin shock as well as hemorrhagic shock.

The compounds of the present invention are also useful in hypoxic and ischemic disease and as anti-ischemic agents for the treatment of, for example, cardiac, renal and cerebral ischemia and reperfusion (such as that occurring following cardiopulmonary bypass surgery), coronary and cerebral vasospasm, and the like.

In addition, the compounds of this invention may also be useful as anti-arrhythmic agents; anti-anginal agents; anti-fibrillatory agents; anti-asthmatic agents; antiatherosclerotic and anti-arteriosclerotic agents; additives to cardioplegic solutions for cardiopulmonary bypasses; adjuncts to thrombolytic therapy; and anti-diarrheal agents. The compounds of this invention may be useful in therapy for myocardial infarction; therapy for peripheral vascular disease (e.g., Raynaud's disease and Takayashu's disease); treatment of cardiac hypertrophy (e.g., hypertrophic cardiomyopathy); treatment of primary pulmonary hypertension (e.g., plexogenic, embolic) in adults and in the newborn and pulmonary hypertension secondary to heart failure, radiation and chemotherapeutic injury, or other trauma; treatment of central nervous system vascular disorders, such as stroke, migraine and subarachnoid hemorrhage; treatment of central nervous system behavioral disorders; treatment of gastrointestinal diseases such as ulcerative colitis, Crohn's disease, gastric mucosal damage, ulcer and ischemic bowel disease; treatment of gall bladder or bile duct-based diseases such as cholangitis; treatment of pancreatitis; regulation of cell growth; treatment of benign prostatic hypertrophy; restenosis following angioplasty or following any procedures including transplantation; therapy for congestive heart failure including inhibition of fibrosis; inhibition of left ventricular dilatation, remodeling and dysfunction; and treatment of hepatotoxicity and sudden death. The compounds of this invention may be useful in the treatment of sickle cell disease including the initiation and/or evolution of the pain crises of this disease; treatment of the deleterious consequences of ET-producing tumors such as hypertension resulting from hemangiopericytoma; treatment of early and advanced liver disease and injury including attendant complications (e.g., hepatotoxicity, fibrosis and cirrhosis); treatment of spastic diseases of the urinary tract and/or bladder; treatment of hepatorenal syndrome; treatment of immunological diseases involving vasculitis such as lupus, systemic sclerosis, mixed cryoglobulinemia; and treatment of fibrosis associated with renal dysfunction and hepatotoxicity. The compounds of this invention may be useful in therapy for metabolic and neurological disorders; cancer; insulin-dependent and non insulin-dependent diabetes mellitus; neuropathy; retinopathy; maternal respiratory distress syndrome; dysmenorrhea; epilepsy; hemorrhagic and ischemic stroke; bone remodeling; psoriasis; and chronic inflammatory diseases such as rheumatoid arthritis, osteoarthritis, sarcoidosis and eczematous dermatitis (all types of dermatitis).

The compounds of this invention can also be formulated in combination with endothelin converting enzyme (ECE) inhibitors, such as phosphoramidon; thromboxane receptor antagonists; potassium channel openers; thrombin inhibitors (e.g., hirudin and the like); growth factor inhibitors such as modulators of PDGF activity; platelet activating factor (PAF) antagonists; angiotensin II (AII) receptor antagonists; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds; neutral endopeptidase (NEP) inhibitors; dual NEP-ACE inhibitors; HMG CoA reductase inhibitors such as pravastatin and mevacor; squalene synthetase inhibitors; bile acid sequestrants such as questran; calcium channel blockers; potassium channel activators; beta-adrenergic agents; antiarrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; and thrombolytic agents such as tissue plasminogen activator (tPA), recombinant tPA, streptokinase, urokinase, prourokinase and anisoylated plasminogen streptokinase activator complex (APSAC). If formulated as a fixed dose, such combination products employ the compounds of this invention within the dosage range described below and the other pharmaceutically active agent within its approved dosage range. The compounds of this invention may also be formulated with, or useful in conjunction with, antifungal and immunosuppressive agents such as amphotericin B, cyclosporins and the like to counteract the glomerular contraction and nephrotoxicity secondary to such compounds. The compounds of this invention may also be used in conjunction with hemodialysis.

The compounds of the invention can be administered orally or parenterally to various mammalian species known to be subject to such maladies, e.g., humans, in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice.

The compounds of the invention may also be administered topically to treat peripheral vascular diseases and as such may be formulated as a cream or ointment.

The compounds of formula I can also be formulated in compositions such as sterile solutions or suspensions for parenteral administration. About 0.1 to 500 milligrams of a compound of formula I is compounded with a physiologically acceptable vehicle, carrier, excipient, binder, preservative, stabilizer, etc., in a unit dosage form as called for by accepted pharmaceutical practice. The amount of active substance in these compositions or preparations is such that a suitable dosage in the range indicated is obtained.

The compounds of the present invention may be prepared as follows.

SCHEME I
Preparation of Compounds of the Formula I

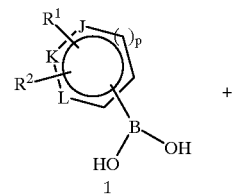

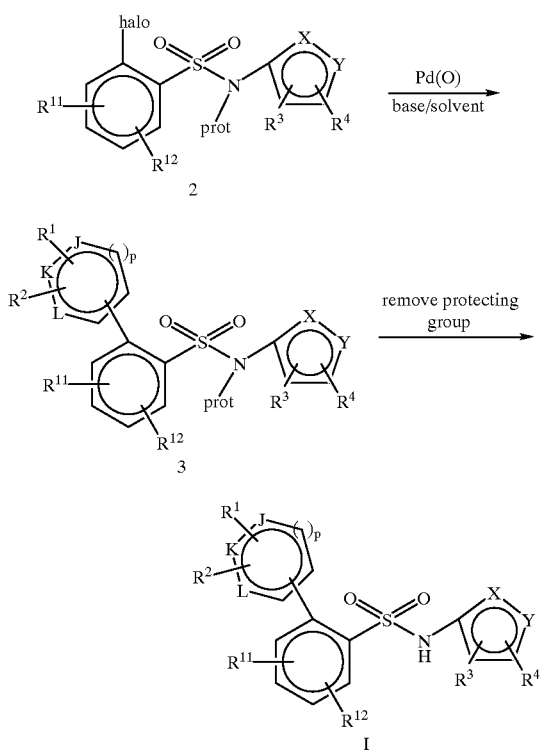

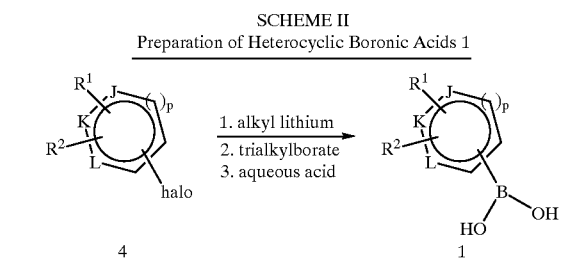

SCHEME II
Preparation of Heterocyclic Boronic Acids 1

As shown in Scheme II, a heterocyclic halide 4 may be converted to a heterocyclic boronic acid 1 by contact with an alkyl lithium compound (such as n-butyl lithium), followed by contact with a trialkylborate (such as triisopropylborate), and finally, by adding an aqueous acid such as aqueous hydrochloric acid. The starting heterocyclic halides 4 are commercially available or may be prepared by methods such as those known in the art.

The halobenzenesulfonamide 2 employed in Scheme I may be prepared as described in European Patent Application 569,193.

The compounds of the formula I may also be synthesized by an alternate route shown in the following Scheme III.

As shown in Scheme I, a heterocyclic boronic acid 1 may be coupled with halobenzenesulfonamide 2 (preferably, a bromobenzenesulfonamide 2), in the presence of a palladium(0) catalyst (such as tetrakis(triphenylphosphine)palladium(0)) and a suitable base (such as aqueous sodium or potassium carbonate) and solvent (such as a mixture of toluene and ethanol), to form the nitrogen-protected intermediate 3. "Prot", as used herein, denotes any suitable nitrogen-protecting group, such as are described in European Patent Application 569,193, incorporated herein by reference. Methoxyethoxymethyl ("MEM") is particularly preferred as "prot". Deprotection of the nitrogen of 3, for example, by contact with HCl in aqueous ethanol when "prot" is MEM, provides a compound of the formula I. It may be desirable, in certain instances, to protect the heteroatoms J, K and/or L to facilitate preparation of the heterocyclic boronic acid 1 (see Scheme II below) and/or the coupling of Scheme I which provides the nitrogen-protected intermediate 3. For example, when J, K or L are N, such a group may be protected by a suitable protecting group such as t-butoxycarbonyl, etc. Also, a compound I may be prepared where, for example, J is $NR^{13}$ and $R^{13}$ is $-SO_2R^{14}$, and a different compound I prepared subsequently by converting $R^{13}$ to hydrogen. In addition, in certain instances, the boronic acid may be replaced with a tin species and/or the halo group may be replaced by a $-OSO_2CF_3$ moiety to perform the Pd-catalyzed coupling reaction.

The heterocyclic boronic acid 1 employed in Scheme I may be prepared as shown in the following Scheme II.

SCHEME III
Alternate Preparation of Compounds of the Formula I

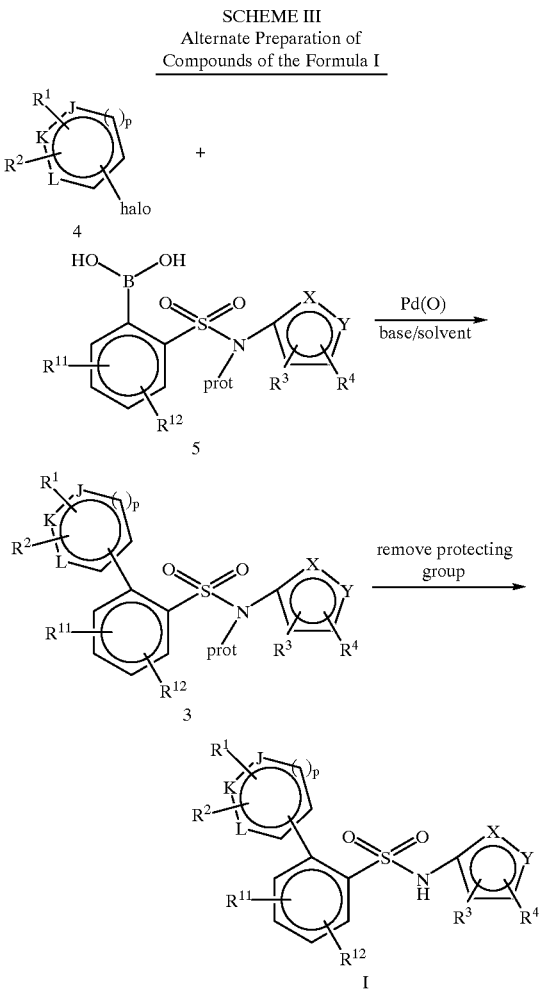

As shown in Scheme III, a compound of the formula I may be prepared by the Pd(O) catalyzed coupling of a heterocyclic halide 4 (such as a heterocyclic bromide or iodide 4) with a benzenesulfonamide boronic acid 5, in the presence of a suitable base and solvent, followed by deprotection of the nitrogen of the compound 3 obtained. The coupling and deprotection reactions may be conducted in a manner similar to those reactions as described in Scheme I.

The benzenesulfonamide boronic acid 5 may be obtained by the method shown in the following Scheme IV, which is analogous to that employed for the preparation of the heterocyclic boronic acid 1 as shown in Scheme II above.

SCHEME IV
Preparation of Benzenesulfonamide
Boronic Acids 5

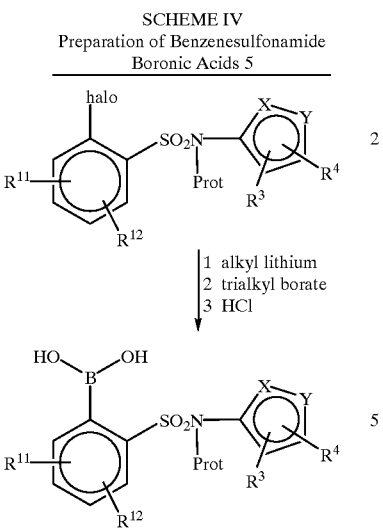

In the above Schemes, specific $R^{11}$ and $R^{12}$ groups may be chosen to be compatible with the reaction conditions shown. Additionally, specific $R^{11}$ and/or $R^{12}$ groups may be converted into alternative $R^{11}$ and/or $R^{12}$ groups, either before or after coupling of heterocyclic boronic acid 1 with halobenzenesulfonamide 2, or heterocyclic halide 4 with benzenesulfonamide boronic acid 5, using methods such as those known in the art.

The methods of Scheme I or Scheme III are preferably selected for preparation of the present compounds based upon the relative ease of availability of the desired heterocyclic-containing starting material 1 or 4. Where the heterocyclic ring is thiophene or indole (such as 3-indole), for example, the present compounds may be prepared by the methods of either Scheme I or Scheme III. Where the heterocyclic ring is pyridine or pyrimidine, for example, the present compounds may be prepared by the method of Scheme III.

The compounds of the present invention and intermediates thereof may also be prepared by methods described in or analogous to those described in U.S. patent application Ser. No. 08/603,975, filed Feb. 20, 1996 by Murugesan et al. (Attorney Docket No. HA662d) entitled "Substituted Biphenyl Isoxazole Sulfonamides" and/or U.S. patent application Ser. No. 60/011,974, filed Feb. 20, 1996 by Polniaszek et al. (Attorney Docket No. HA689*) entitled "Methods for the Preparation of Biphenyl Isoxazole Sulfonamides", each incorporated herein by reference in its entirety.

The invention will now be further described by the following working examples, which are preferred embodiments of the invention. These examples are intended to be illustrative rather than limiting.

EXAMPLE 1

N-(3,4-Dimethyl-5-isoxazolyl)-2-(2-thienyl)benzenesulfonamide

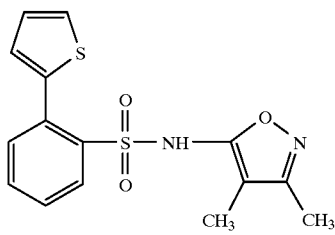

A. N-(3,4-Dimethyl-5-isoxazolyl)-N-[(2-methoxyethoxy)methyl]-2-(2-thienyl)benzenesulfonamide To a solution of 2-bromo-N-(3,4-dimethyl-5-isoxazolyl)-N-[(2-methoxyethoxy)methyl]benzenesulfonamide (545 mg, 1.3 mmol, prepared as described in European Patent Application No. 569,193), 2-boronothiophene (166 mg, 1.3 mmol) in 9.5 ml of toluene and 7.6 ml of 95% ethanol (EtOH) under argon, tetrakis(triphenylphosphine)palladium (0) (90 mg, 0.078 mmol) was added, followed by 5.7 ml of 2M aq. sodium carbonate. The reaction mixture was heated at 80° C. for 6.5 hrs, cooled and diluted with 30 ml of ethyl acetate (EtOAc). The organic liquid was separated and washed with 15 ml $H_2O$ and 15 ml of brine, dried and concentrated. The residue was chromatographed on silica gel using 4:1 hexane/EtOAc to afford the title product of this step (230 mg, 42%) as a colorless gum. $R_f$=0.53, silica gel, 1:1 Hexane/EtOAc.

B. N-(3,4-Dimethyl-5-isoxazolyl)-2-(2-thienyl)benzenesulfonamide

To a solution of the title product of Step (A) (225 mg, 0.53 mmol) in 10 ml of 95% EtOH, 10 ml of 6 N aq. HCl was added and refluxed for 2.5 hrs. The reaction mixture was concentrated to about 10 ml and extracted with 3×15 ml of EtOAc. The organic extracts were washed with 10 ml of brine and dried and concentrated. The residue was chromatographed on silica gel using 2:1 hexane/EtOAc to provide the title product of this Example (149 mg, 84%) as a white solid. m.p. 112–115° C.; Rf=0.32, silica gel, 1:1 hexane/EtOAc.

Analysis calculated for $C_{15}H_{14}N_2O_3S_2$ Calc'd: C, 53.88; H, 4.22; N, 8.38; S, 19.17. Found: C, 53,45; H, 4.22; N, 8.29; S, 18.78.

EXAMPLE 2

N-(3,4-Dimethyl-5-isoxazolyl)-2-(3-thienyl)benzenesulfonamide

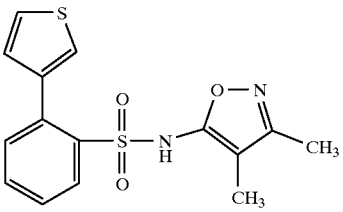

A. N-(3,4-Dimethyl-5-isoxazolyl)-N-[(2-methoxyethoxy)methyl]-2-(3-thienyl)benzenesulfonamide To a solution of 0.3 g (0.715 mmol) of 2-bromo-N-(3,4-dimethyl-5-isoxazolyl)-N-[(2-methoxyethoxy)methyl]benzenesulfonamide and 0.041 g (0.035 mmol) of tetrakis (triphenylphosphine)palladium(0) in 12 mL of toluene under argon, 6 mL of 2M aq. sodium carbonate was added followed by 0.11 g (0.858 mmol) of 3-boronothiophene added in 8 mL of 95% EtOH. The mixture was refluxed for 10 hrs and then diluted with 100 mL of water and extracted with 3×50 mL of EtOAc. The combined organic extracts were washed once with 100 mL of brine and dried and evaporated. The residue was chromatographed on 20 g of silica gel using Hexanes/EtOAc 2:1 to afford 0.18 g (60%) of the title product of this step as a light brown gum.

B. N-(3,4-Dimethyl-5-isoxazolyl)-2-(3-thienyl)benzenesulfonamide

To a solution of 0.16 g (0.38 mmol) of the title product of Step (A) in 6 mL of 95% EtOH, 6 mL of 6N aq. HCl was added and refluxed for 2 hrs. The mixture was then concentrated and diluted with 25 mL of water and the solution was then extracted with 3×20 mL of EtOAc. The combined organic extracts were then washed once with water and dried and evaporated (0.16 g). The residue was chromatographed on 25 g of silica gel using Hexanes/EtOAc 3:2 to provide 0.10 g (78%) of the title product of this Example as light brown prisms. m.p. 147–148° C.

|  | Anal. Calc. For $C_{15}H_{14}N_2O_3S_2$: | | | |
|---|---|---|---|---|
|  | C, 53.88; | H, 4.22; | N, 8.38; | S, 19.17 |
| Found: | C, 53.57; | H, 4.13; | N, 8.17; | S, 18.86. |

EXAMPLE 3

N-(3,4-Dimethyl-5-isoxazolyl)-2-(2-pyridinyl)benzenesulfonamide

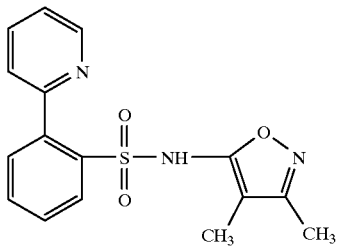

A. 2-Borono-N-(3,4-dimethyl-5-isoxazolyl)-N-[(2-methoxyethoxy)methyl]benzenesulfonamide To a solution of 2-bromo-N-(3,4-dimethyl-5-isoxazolyl)-N-[(2-methoxyethoxy)methyl]benzenesulfonamide (1.69 g, 4.03 mmol) in 40 ml diethyl ether (Et$_2$O) and 10 ml tetrahydrofuran (THF) at −78° C., n-butyl lithium (n-BuLi, 2 M in cyclohexane, 2.52 ml, 5.04 mmol) was added dropwise. The resulting solution was stirred at −78° C. for 15 min and triisopropylborate (1.52 g, 8.06 mmol) was added. The reaction was warmed to room temperature and stirred at room temperature overnight, before hydrolysis with 40 ml 10% aqueous HCl at 0° C. The aqueous layer was extracted with 2×30 ml EtOAc. The combined organic extracts were extracted with 3×40 ml 1 N NaOH and the combined NaOH extracts were acidified to pH 2 with 6N HCl. This solution was extracted with 3×40 ml EtOAc, and the extracts were washed once with 20 ml brine, dried (MgSO$_4$) and concentrated to give the title product of this step (600 mg, 39%) as a light yellow solid. R$_f$=0.42, silica gel, 30:1 CHCl$_3$/methanol (MeOH).

B. N-(3,4-Dimethyl-5-isoxazolyl)-N-[(2-methoxyethoxy)methyl]-2-(2-pyridinyl)benzenesulfonamide To a solution of the title product of Step (A) (320 mg, 0.83 mmol), 2-bromopyridine (658 mg, 4.16 mmol) in 7.5 ml of toluene and 6 ml of 95% EtOH under argon, tetrakis(triphenylphosphine)palladium(0) (96 mg, 0.083 mmol) was added and followed by 4.5 ml of 2M aq. sodium carbonate. The reaction mixture was heated at 75° C. for 4 hrs, cooled and diluted with 40 ml of EtOAc. The organic liquid was separated and washed with 10 ml H$_2$O and 10 ml brine, dried and concentrated. The residue was chromatographed on silica gel using 1:2.5 hexane/EtOAc to afford the title product of this step (227 mg, 65%) as a colorless gum. R$_f$=0.27, silica gel, 1:5 Hexane/EtOAc.

C. N-(3,4-Dimethyl-5-isoxazolyl)-2-(2-pyridinyl)benzenesulfonamide

To a solution of the title product of Step (B) (225 mg, 0.54 mmol) in 6 ml of 95% EtOH, 6 ml of 6 N aq. HCl was added and refluxed for 1 hr and 10 min. The reaction mixture was concentrated and the pH of the solution was adjusted to 8 using sodium bicarbonate solution. It was then reacidified to pH 5 with glacial acetic acid. The mixture was extracted with 3×40 ml EtOAc. The organic liquid was washed with 10 ml H$_2$O and 10 ml of brine and dried and concentrated to give a white solid. Crystallization from EtOAc/hexane provided the title product of this Example (136 mg, 76%) as white crystals. m.p. 136–137° C., Rf=0.71, silica gel, 1:5 hexane/EtOAc.

Analysis calculated for $C_{16}H_{15}N_3O_3S$ Calc'd: C, 58.35; H, 4.59; N, 12.76; S, 9.73. Found: C, 58.30; H, 4.41; N, 12.66; S, 9.59.

EXAMPLE 4

N-(3,4-Dimethyl-5-isoxazolyl)-2-[1-(phenylsulfonyl)-1H-indol-3-yl]benzenesulfonamide

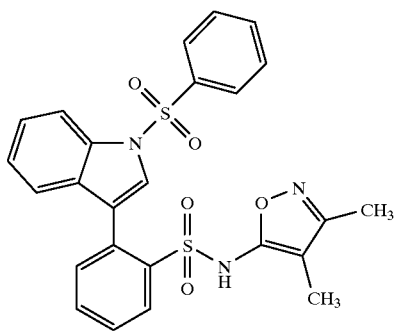

A. 1-(Phenylsulfonyl)-1H-indole

A 2.5M solution of n-BuLi (10 ml; 25 mmol) was added dropwise over 20 minutes to a solution of 1H-indole (2.75 g; 23.5 mmol) in 25 ml of THF at −78° C. After stirring at −78° C. for 15 minutes, the reaction mixture was allowed to warm to 0° C. over 1 hour. After recooling to −78° C., benzenesulfonyl chloride (3.35 ml; 26.25 mmol) was added dropwise over 20 minutes, maintaining the internal temperature below −70° C. After warming to room temperature and stirring 18 hours, the reaction mixture was poured into 60 ml of 2% NaHCO$_3$ solution. The resulting mixture was extracted with ether (3×50 ml) and the combined organic layer was washed with saturated NaHCO$_3$ solution (50 ml), water (2×50 ml) and brine (50 ml). After drying over MgSO$_4$, the organic layer was concentrated to afforded an amber oil which was triturated with ~10 ml of hexane:ether, 2:1. Filtration of the resulting solid and rinsing with hexane afforded 4.27 g (71%) of the title product of this step as a light pink crystalline solid.

The title product of this step is also commercially available (Aldrich). The following is a preferred procedure for purification of the commercially available material before use. Crude, dark brown (1-phenylsulfonyl)indole (~3 g) was dissolved in a minimal volume of hot ether. Decolorizing carbon was added and the mixture was filtered hot through celite. After adding hexane until the solution became cloudy, the ether was removed in vacuo. A light yellow oil separated and the mixture was brought to reflux. Ether was added portionwise to homogeneity. Seeds of the title product of this step were added and the mixture was allowed to cool slowly to 5° C. Filtration and drying afforded 2.25 g of the pure title product of this step as a slightly off-white crystalline solid.

B. 3-Bromo-1-(phenylsulfonyl)-1H-indole

A solution of bromine (0.33 ml; 6.3 mmol) in 5 ml of $CCl_4$ was added dropwise over 20 minutes to a solution of the title product of Step (A) (1.54 g; 6 mmol) in 12 ml of $CCl_4$. The resulting red solution was stirred for 4 hours at room temperature, after which time it was poured into 25 ml of saturated $NaHCO_3$ solution. The layers were separated and the organic phase was washed with saturated $NaHCO_3$ solution (25 ml), 10% $Na_2S_2O_3$ (25 ml), water (25 ml), and brine (25 ml). After drying ($MgSO_4$) and decolorizing (Darco), the organic phase was concentrated to afford 1.92 g (95%) of the title product of this step as a colorless crystalline solid.

C. 3-Borono-1-(phenylsulfonyl)-1H-indole

A 1.7 M solution of tert-butyl lithium (t-BuLi) in pentane (3.8 ml; 6.45 mmol) was added over ~5 minutes, to a solution of the title product of Step (B) (1 g; 3 mmol) in THF at –100° C. The temperature was kept below –84° C. during the addition. After stirring 5 minutes at –100° C., trimethylborate was added in one portion and the reaction mixture was allowed to warm to room temperature over 4 hours. At this time, 10 ml of 10% HCl was added and the mixture was extracted with methylene chloride (3×30 ml). The combined organic layers were washed with water (3×30 ml) and brine (30 ml). Drying ($MgSO_4$), decolorizing (Darco) and concentration afforded a tan foam. Due to apparent decomposition at room temperature, the foam was stored at –80° C. overnight. The residue was then partitioned between ether (20 ml) and 0.5 $\underline{N}$ NaOH (20 ml). The purple ether layer was extracted with 10 ml of 0.5N NaOH. The combined green basic layer was washed with ether (20 ml), acidified to pH 2 with saturated $KHSO_4$ solution to afford a purple mixture, which was extracted with methylene chloride (2×30 ml). Drying ($MgSO_4$) and concentration afforded 623 mg (69%) of the title product of this step as a purple foam.

D. N-(3,4-Dimethyl-5-isoxazolyl)-N-[(2-methoxyethoxy)methyl]-2-[1-(phenylsulfonyl)-1H-indol-3-yl]benzenesulfonamide After purging a solution of 2-bromo-N-(3,4-dimethyl-5-isoxazolyl)-N-[(2-methoxyethoxy)methyl]benzenesulfonamide (595 mg; 1.42 mmol) in 14 ml of toluene and 12 ml of EtOH with argon for 20 minutes, the title product of Step (C) (600 mg; 1.99 mmol) was added followed by 2M $Na_2CO_3$ (10 ml; previously purged with argon) and tetrakis(triphenylphosphine)palladium(0) (200 mg). The heterogeneous mixture was heated to 75–80° C. for 5 hrs. After cooling to room temperature, the reaction mixture was partitioned between ethyl acetate (50 ml) and water (25 ml). The aqueous layer was extracted with an additional 25 ml of ethyl acetate and the combined organic layers were washed with water (25 ml) and brine (25 ml). After drying ($MgSO_4$) and decolorizing (Darco), the green solution was concentrated to afford a dark green residue which was chromatographed on a 5×12 cm silica gel column, using 2 L EtOAc:hexanes, 1:3, 1 L EtOAc:hexanes, 3:7 and 1 L EtOAc:hexanes, 35:65 as the mobile phase. The pure fractions were concentrated to afford 379 mg (45%) of the title product of this step as a blue-green foam.

Mass Spec. CI+ ions (relative intensity): M+H=596 (30).

E. N-(3,4-Dimethyl-5-isoxazolyl)-2-[1-(phenylsulfonyl)-1H-indol-3-yl]benzenesulfonamide A mixture of the title product of Step (D) (350 mg; 0.59 mmol), 6N HCl (6 ml) and EtOH (6 ml) was refluxed for 3 hours. After cooling, the reaction mixture was partitioned between EtOAc (50 ml) and water (25 ml). The aqueous layer was extracted with EtOAc (50 ml) and the combined organic layers were washed with brine (2×50 ml). The blue solution was dried ($MgSO_4$) and concentrated to a dark blue residue. Attempts at purifying this residue using silica gel chromatography were unsuccessful. The material isolated from combining all fractions was subjected to reverse phase preparative HPLC. (30×500 mm ODS column; S-3; two injections-30 and 150 mg; stepwise gradient 75–83% $MeOH/H_2O+0.1\%$ trifluoroacetic acid (TFA); 2% increments every 5 minutes; 35 ml/minute flow rate.) The pure fractions were concentrated and the residues were partitioned between EtOAc and water. The organic layer was washed with water and brine. Drying ($MgSO_4$), concentration and co-evaporation from $MeOH/H_2O$ afforded 130 mg (43%) of the title product of this Example as a light yellow amorphous solid. mp 85–95° C. (dec.); Rf=0.63, EtOAc (UV detection).

| Analysis calc. for $C_{25}H_{21}N_3O_5S_2 \cdot 0.2 \ CF_3COOH$: | | |
|---|---|---|
| | C, 57.52; | H, 4.03; | N, 7.92; |
| Found | C, 57.84; | H, 3.62; | N, 7.75. |

EXAMPLE 5

N-(3,4-Dimethyl-5-isoxazolyl)-2-(1H-indol-3-yl)benzenesulfonamide

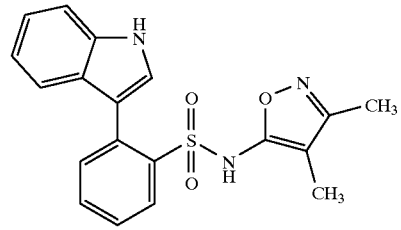

A solution of the title product of Example 4 (110 mg; 0.217 mmol) in 0.7 ml of 1N KOH and 0.7 ml of MeOH was heated to 50° C. for 24 hrs. After partitioning the reaction mixture between EtOAc (25 ml) and saturated $KHSO_4$ (25 ml), the organic layer was washed with brine (25 ml), dried ($MgSO_4$) and concentrated. The residue was chromatographed on a 2.5×15 cm silica gel column, using a stepwise gradient from $CH_2Cl_2$ to 1% $MeOH/CH_2Cl_2$ in 0.25% increments and 200 ml portions. The purest fractions were concentrated and the solid residue was recrystallized twice from EtOAc/hexanes to afford 62 mg (78%) of the title product of this Example as a colorless crystalline solid. mp 184–186° C.; Rf=0.24, 5% $MeOH/CH_2Cl_2$ (UV detection).

| Analysis calc. for $C_{19}H_{17}N_3O_3S.0.43\ H_2O$: | | |
|---|---|---|
| C, 60.83; | H, 4.80; | N, 11.20; |
| Found    C, 61.00; | H, 4.53; | N, 11.03. |

EXAMPLE 6

N-(3,4-Dimethyl-5-isoxazolyl)-2-[1-(phenylsulfonyl)-1H-indol-2-yl]benzenesulfonamide

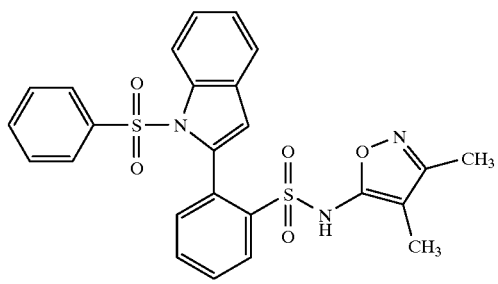

A. 2-Iodo-1-(phenylsulfonyl)-1H-indole

A solution of 1-(phenylsulfonyl)-1H-indole (1.35 g; 5.24 mmol, prepared as in Step (A) of Example 4) in 10 ml of THF was added dropwise over 10 minutes to a −78° C. solution of lithium diisopropylamide (LDA) in 15 ml of THF prepared from diisopropylamine (0.86 ml; 5.9 mmol) and 2.5 M n-BuLi (2.2 ml; 5.5 mmol). After stirring 1 hr at −78° C., the mixture was allowed to warm to 0° C. over 1 hr. After recooling to −78° C., iodine (1.78 g; 6.81 mmol) was added in one portion and the resulting mixture was stirred 2 hr at −78° C. and 18 hrs at room temperature. The reaction mixture was partitioned between EtOAc (75 ml) and saturated $NaHCO_3$ solution (50 ml). The organic layer was washed with saturated $NaHSO_3$ solution (2×50 ml) and brine (50 ml). Drying ($MgSO_4$), decolorizing (Darco) and concentration afforded a ruby colored oil which was crystallized from ether/hexane to afford 965 mg (48%) of the title product of this step as a tan crystalline solid.

B. 2-Borono-N-(3,4-dimethyl-5-isoxazolyl)-N-[(2-methoxyethoxy)methyl]benzenesulfonamide A 1.7 M solution of t-BuLi in pentane (5.0 ml; 8.50 mmol) was added over ~10 minutes to a solution of 2-bromo-N-(3,4-dimethyl-5-isoxazolyl)-N-[(2-methoxyethoxy)methyl]benzenesulfonamide (1.62 g; 3.86 mmol) in THF at −100° C. The temperature was kept below −80° C. during the addition. After stirring 5 minutes at −100° C., trimethylborate (0.53 ml; 4.63 mmol) was added in one portion and the reaction mixture was allowed to warm to room temperature over several hours. At this time, 15 ml of 10% HCl was added and the mixture was extracted with methylene chloride (3×50 ml). The combined organic layers were washed with water (50 ml) and brine (50 ml). Drying ($MgSO_4$), and concentration afforded a yellow oil. The residue was then partitioned between ether (50 ml) and 0.5 N NaOH (20 ml). The ether layer was extracted with 10 ml of 0.5N NaOH. The combined basic layers were washed with ether (50 ml), acidified to pH ~1.5 with saturated $KHSO_4$ solution and extracted with methylene chloride (3×50 ml). Drying ($MgSO_4$) and concentration afforded 1.04 g (70%) of the title product of this step as a light yellow foamy oil.

C. N-(3,4-Dimethyl-5-isoxazolyl)-N-[(2-methoxyethoxy)methyl]-2-[1-(phenylsulfonyl)-1H-indol-2-yl]benzenesulfonamide Tetrakis(triphenylphosphine)palladium(0) (230 mg; 10 mol %) was added to a degassed solution of the title product of Step (A) (766 mg; 2 mmol) and the title product of Step (B) (900 mg; 2.34 mmol) in 10 ml of toluene and 8.5 ml of EtOH under argon. After adding 7 ml of 2M $Na_2CO_3$, the heterogeneous mixture was heated to 85° C. for 5 hrs with vigorous stirring. At this time, an additional amount of the title product of Step (B) (100 mg; 0.26 mmol) was added and the mixture was heated an additional 2 hrs. After cooling to room temperature, the reaction mixture was partitioned between ethyl acetate (75 ml) and water (50 ml). The organic layer was washed with brine (50 ml), dried ($MgSO_4$), and concentrated to afford a yellow residue which was chromatographed on a 5×20 cm silica gel column, using 4 L EtOAc:Hexanes, 3:7, 2 L EtOAc:hexanes, 4:6 and 1 L EtOAc:Hexanes, 1:1 as the mobile phase. The pure fractions were concentrated to afford 222 mg (19%) of the title product of this step as a light yellow foam.

Mass Spec. CI+ ions (relative intensity): M+H=596 (20), 520 (100).

D. N-(3,4-Dimethyl-5-isoxazolyl)-2-[1-(phenylsulfonyl)-1H-indol-2-yl]benzenesulfonamide A mixture of the title product of Step (C) (210 mg; 0.35 mmol), 6N HCl (5 ml) and EtOH (5 ml) was refluxed for 1.5 hours. A solid began precipitating during the reaction. After slowly cooling to 5° C., the suspension was filtered and the solid was washed with water. Drying afforded 154 mg (87%) of the title product of this Example as a cream colored solid. mp 207–209° C. (dec.; darkened at 196° C.); Rf=0.50, EtOAc (UV detection).

| Analysis calc. for $C_{25}H_{21}N_3O_5S_2.0.11\ H_2O$: | | |
|---|---|---|
| C, 58.92 | H, 4.20; | N, 8.25; |
| Found    C, 59.14; | H, 4.07; | N, 8.03. |

EXAMPLE 7

N-(3,4-Dimethyl-5-isoxazolyl)-2-(2-pyrimidinyl)benzenesulfonamide

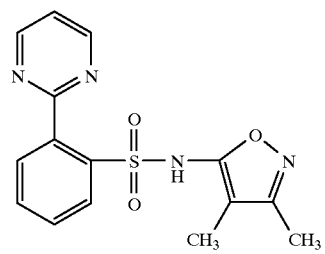

A. N-(3,4-Dimethyl-5-isoxazolyl)-N-[(2-methoxyethoxy)methyl]-2-(2-pyrimidinyl)benzenesulfonamide To a solution of 2-borono-N-(3,4-dimethyl-5-isoxazolyl)-N-[(2-methoxyethoxy)methyl]benzenesulfonamide (280 mg, 0.73 mmol, prepared as described in Step (A) of Example 3), 2-bromopyrimidine (348 mg, 2.19 mmol) in 7 ml of toluene and 5.6 ml of 95% EtOH under argon, tetrakis(triphenylphosphine)palladium(0) (84 mg, 0.073 mmol) was added, followed by 4.2 ml of 2M aq. sodium carbonate. The reaction mixture was heated at 75° C. for 3.5 hrs, cooled and diluted with 40 ml of EtOAc. The organic liquid was separated and washed with 10 ml $H_2O$ and 10 ml brine, dried and concentrated. The residue was chromatographed on silica gel using 1:2 hexane/EtOAc to afford the title product of this step (150 mg, 49%) as a colorless gum. R_f=0.37, silica gel, 1:5 Hexane/EtOAc.

B. N-(3,4-Dimethyl-5-isoxazolyl)-2-(2-pyrimidinyl)benzenesulfonamide

To a solution of the title product of Step (A) (150 mg, 0.36 mmol) in 5 ml of 95% EtOH, 5 ml of 6 N aq. HCl was added and refluxed for 1 hr and 10 min. The reaction mixture was concentrated and the pH of the solution was adjusted to 8 using sodium bicarbonate solution. It was then reacidified to pH 5 with glacial acetic acid. The mixture was extracted with 3×40 ml EtOAc. The organic liquid was washed with 10 ml H$_2$O and 10 ml brine and dried and concentrated. The residue was chromatographed on silica gel using 1:2 hexane/EtOAc to afford the title product of this Example (86 mg, 73%) as a light yellow solid. m.p. 160–162° C., Rf=0.62, silica gel, 1:5 hexane/EtOAc.

Analysis calculated for C$_{15}$H$_{14}$N$_4$O$_3$S·0.72H$_2$O Calc'd: C, 52.49; H, 4.53; N, 16.32; S, 9.34. Found: C, 52.54; H, 4.25; N, 16.27; S, 9.49.

EXAMPLE 8

N-(3,4-Dimethyl-5-isoxazolyl)-2-(3-pyridinyl)benzenesulfonamide

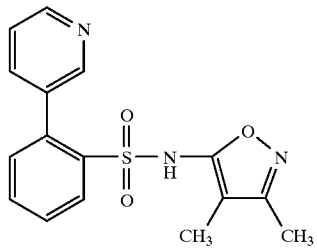

A. N-(3,4-Dimethyl-5-isoxazolyl)-N-[(2-methoxyethoxy)methyl]-2-(3-pyridinyl)benzenesulfonamide To a solution of 2-borono-N-(3,4-dimethyl-5-isoxazolyl)-N-[(2-methoxyethoxy)methyl]benzenesulfonamide (270 mg, 0.7 mmol, prepared as described in Step (A) of Example 3), 3-bromopyridine (553 mg, 3.5 mmol) in 7 ml of toluene and 5.6 ml of 95% EtOH under argon, tetrakis(triphenylphosphine)palladium(0) (81 mg, 0.07 mmol) was added and followed by 4.2 ml of 2M aq. sodium carbonate. The reaction mixture was heated at 75° C. for 3.5 hrs, cooled and diluted with 40 ml of EtOAc. The organic liquid was separated and washed with 10 ml H$_2$O and 10 ml brine, dried and concentrated. The residue was chromatographed on silica gel using 1:2.5 hexane/EtOAc to afford the title product of this step (220 mg, 75%) as a colorless gum. R_f=0.18, silica gel, 1:5 Hexane/EtOAC.

B. N-(3,4-Dimethyl-5-isoxazolyl)-2-(3-pyridinyl)benzenesulfonamide

To a solution of the title product of Step (A) (218 mg, 0.52 mmol) in 6 ml of 95% EtOH, 6 ml of 6 N aq. HCl was added and refluxed for 1 hr and 10 min. The reaction mixture was concentrated and the pH of the solution was adjusted to 8 using sodium bicarbonate solution. It was then reacidified to pH 5 with glacial acetic acid. The mixture was extracted with 3×40 ml EtOAc. The organic liquid was washed with 10 ml H$_2$O and 10 ml brine, dried and concentrated. The residue was chromatographed on silica gel using 100:1.5 CH$_2$Cl$_2$/MeOH to afford the title product of this Example (157 mg, 91%) as a light yellow solid. m.p. 147–150° C., Rf=0.18, silica gel, 1:5 hexane/EtOAc.

Analysis calculated for C$_{16}$H$_{15}$N$_3$O$_3$S·0.25H$_2$O Calc'd: C, 57.57; H, 4.68; N, 12.59; S, 9.60. Found: C, 57.89; H, 4.53; N, 12.27; S, 9.56.

EXAMPLE 9

N-(3,4-Dimethyl-5-isoxazolyl)-2-(1H-indol-2-yl)benzenesulfonamide

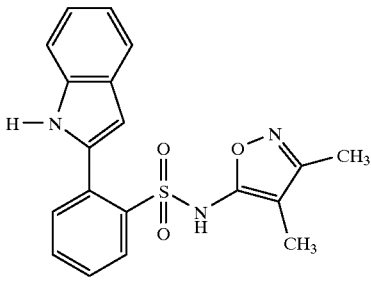

A mixture of the title product of Example 6 (125 mg; 0.25 mmol) in 2 ml of 1N KOH and 2 ml of MeOH was heated to 55° C. for 72 hrs. After partitioning the reaction mixture between EtOAc (50 ml) and saturated KHSO$_4$ (50 ml), the organic layer was washed with brine (30 ml), dried (MgSO$_4$) and concentrated. The residue was chromatographed on a 2.5×15 cm silica gel column, using EtOAc:Hexanes, 1:1 as the mobile phase. The pure fractions were concentrated to afford 6 mg of the title product of this Example as a yellow solid. The mixed fractions were combined and rechromatographed on a 2×20 cm silica gel column using a stepwise gradient from 20% EtOAc/Hexanes to EtOAc in 10% increments and 300 ml portions, followed by 300 ml of 5% MeOH/CH$_2$Cl$_2$. The pure fractions were concentrated and combined with material from the first chromatography to afford 25 mg (27%) of the title product of this Example as a yellow powder. mp 172–175° C.; Rf=0.38, EtOAc (UV detection).

What is claimed is:

1. A compound of the formula

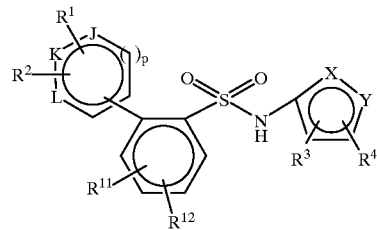

or an enantiomer, diastereomer, or pharmaceutically acceptable salt thereof wherein:

X is O;

Y is N;

R$^3$ and R$^4$ are each independently lower alkyl;

the ring system

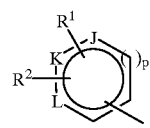

is selected from the group consisting of

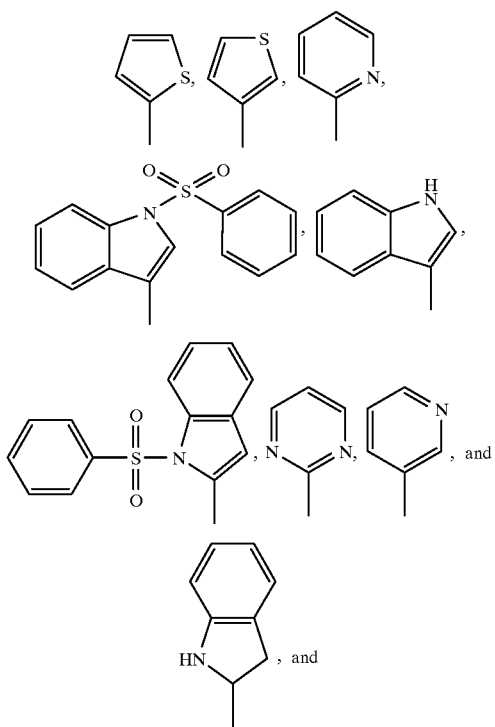

$R^{11}$ and $R^{12}$ are both hydrogen.

2. A compound of claim 1, wherein $R^3$ and $R^4$ are each methyl.

3. A compound of claim 1 selected from the group consisting of:
N-(3,4-Dimethyl-5-isoxazolyl)-2-(2-thienyl)benzenesulfonamide;
N-(3,4-Dimethyl-5-isoxazolyl)-2-(3-thienyl)benzenesulfonamide;
N-(3,4-Dimethyl-5-isoxazolyl)-2-(2-pyridinyl)benzenesulfonamide;
N-(3,4-Dimethyl-5-isoxazolyl)-2-[1-(phenylsulfonyl)-1H-indol-3-yl]benzenesulfonamide;
N-(3,4-Dimethyl-5-isoxazolyl)-2-(1H-indol-3-yl)benzenesulfonamide;
N-(3,4-Dimethyl-5-isoxazolyl)-2-[1-(phenylsulfonyl)-1H-indol-2-yl]benzenesulfonamide;
N-(3,4-Dimethyl-5-isoxazolyl)-2-(2-pyrimidinyl)benzenesulfonamide;
N-(3,4-Dimethyl-5-isoxazolyl)-2-(3-pyridinyl)benzenesulfonamide; and
N-(3,4-Dimethyl-5-isoxazolyl)-2-(1H-indol-2-yl)benzenesulfonamide.

4. A method of treating endothelin-related disorders in a mammal, which comprises administering to said mammal an effective endothelin-related disorder treating amount of a compound of claim 1.

5. A method of treating hypertension, which comprises administering an effective hypertension treating amount of a compound of claim 1.

6. A method of treating pulmonary hypertension, which comprises administering an effective pulmonary hypertension treating amount of a compound of claim 1.

7. A method of treating renal, glomerular or mesangial cell disorders, which comprises administering an effective renal, glomerular or mesangial cell disorder treating amount of a compound of claim 1.

8. A method of treating endotoxemia, which comprises administering an effective endotoxemia treating amount of a compound of claim 1.

9. A method of treating ischemia, which comprises administering an effective ischemia treating amount of a compound of claim 1.

10. A method of inhibiting cell growth, which comprises administering an effective cell growth inhibiting amount of a compound of claim 1.

11. A method of treating atherosclerosis, which comprises administering an effective atherosclerosis treating amount of a compound of claim 1.

12. A method of treating restenosis, which comprises administering an effective restenosis treating amount of a compound of claim 1.

13. A method of treating subarachnoid hemorrhage, which comprises administering an effective subarachnoid hemorrhage treating amount of a compound of claim 1.

14. A method of treating benign prostatic hypertrophy, which comprises administering a benign prostatic hypertrophy treating amount of a compound of claim 1.

15. A method of treating congestive heart failure in a mammal, which comprises administering to said mammal an effective congestive heart failure treating amount of a compound of claim 1.

16. The method of claim 13, wherein said compound of claim 1 is used in combination with at least one angiotensin II (AII) receptor antagonist, renin inhibitor, angiotensin converting enzyme (ACE) inhibitor, or dual neutral endopeptidase (NEP)-ACE inhibitor.

17. A pharmaceutical composition for the treatment of an endothelin-related disorder, comprising a compound of claim 1 in an amount effective therefor and a physiologically acceptable vehicle or carrier.

18. A pharmaceutical composition of claim 17, further comprising at least one angiotensin II (AII) receptor antagonist, renin inhibitor, angiotensin converting enzyme (ACE) inhibitor, or dual neutral endopeptidase (NEP)-ACE inhibitor.

* * * * *